United States Patent [19]
Villeponteau et al.

[11] Patent Number: 5,580,726
[45] Date of Patent: Dec. 3, 1996

[54] METHOD AND KIT FOR ENHANCED DIFFERENTIAL DISPLAY

[75] Inventors: Bryant Villeponteau; Junli Feng, both of San Carlos; Walter Funk, Union City; Maarten H. K. Linskens, Palo Alto, all of Calif.

[73] Assignee: Geron Corporation, Menlo Park, Calif.

[21] Appl. No.: 235,180

[22] Filed: Apr. 29, 1994

[51] Int. Cl.$^6$ ................................ C12Q 1/68; C12P 19/34
[52] U.S. Cl. ................................................. 435/6; 435/91.2
[58] Field of Search ...................... 435/6, 92.1; 935/77, 935/78

[56] References Cited

U.S. PATENT DOCUMENTS

| | | | |
|---|---|---|---|
| 5,066,584 | 11/1991 | Gyllensten et al. | 435/91.2 |
| 5,262,311 | 11/1993 | Pardee et al. | 435/91.2 |
| 5,489,508 | 2/1996 | West et al. | 435/6 |

FOREIGN PATENT DOCUMENTS 9318176  9/1993  WIPO.

OTHER PUBLICATIONS

Ito et al., "Fluorescent differential display: arbitrarily primed RT–PCR fingerprinting on an automated DNA sequencers", *FEBS Letters* 351:231–236 (1994).

Joseph et al., "Molecular Cloning of a Novel mRNA (Neuronatin) That Is Highly Expressed in Neonatal Mammalian Brain", *Biochem. Biophys. Res. Comm.* 201:1227–1234 (1994).

Kumar et al., "Expression of interleukin 1–inducible genes and production of interleukin 1 by aging human fibroblasts", *Proc. Nat'l Acad. Sci.* 89:4683–4687 (1992).

Linskens et al., "Cataloging altered gene expression in young and senescent cells using enhanced differential display", *Nucleic Acid Research* 23:3244–3251 (1995).

Mou et al., "Improvements to the Differential Display Method For Gene Analysis", *Biochem. Biophys. Res. Comm.* 199:564–569 (1994).

West et al., "Replicative Senescence of Human Skin Fibroblasts Correlates with a Loss of Regulation and Overexpression of Collagenase Activity", *Experimental Cell Research* 184:138–147 (1989).

Zimmerman and Schultz, "Analysis of gene expression in the preimplantation mouse embryo: Use of mRNA differential display", *Proc. Nat'l Acad. Sci.* 91:5456–5460 (1994).

Liang, et al., "Distribution and cloning of eukaryotic mRNAs by means of differential display: refinements and optimization", 21 *Nucl. Acids Res.* 3269, 1993.

Torres et al Enferm. Infecc. Microbiol. Clin. 10:345–8 (1992).

PNAS 85:8998–9002 (1988).

Clontech Catalog (1993)–Quick –Clone p. 38.

*Primary Examiner*—W. Gary Jones
*Assistant Examiner*—Eggerton Campbell
*Attorney, Agent, or Firm*—Kevin Kaster; Richard J. Warburg; Amy S. Hellenkamp

[57] ABSTRACT

An improved method for detecting and isolating differentially expressed mRNAs which comprises using first oligonucleotide primers for reverse transcription of mRNAs and both the first oligonucleotide primers and second oligonucleotide primers for amplification of the resultant cDNAs. The improvement of this method comprises providing first and second oligonucleotide primers with a length of at least 21 oligonucleotides. The method further comprises using a two-step PCR amplification, wherein non-stringent conditions are used for the first 1 to 4 cycles, and stringent conditions are used for the next 16 to 22 cycles. This highly reproducible method will permit the preparation of comprehensive catalogs of gene expression for any given cell type.

14 Claims, 4 Drawing Sheets

5' primers

| | | |
|---|---|---|
| 0 | 5'-CGG GAA GCT TAT CGA CTC CAA G | SEQ ID NO. 7 |
| 1 | 5'-CGG GAA GCT TTA GCT AGC ATG G | SEQ ID NO. 8 |
| 2 | 5'-CGG GAA GCT TGC TAA GAC TAG C | SEQ ID NO. 9 |
| 3 | 5'-CGG GAA GCT TTG CAG TGT GTC A | SEQ ID NO. 10 |
| 4 | 5'-CGG GAA GCT TGT GAC CAT TGC A | SEQ ID NO. 11 |
| 5 | 5'-CGG GAA GCT TGT CTG CTA GGT A | SEQ ID NO. 12 |
| 6 | 5'-CGG GAA GCT TGC ATG GTA GTC T | SEQ ID NO. 13 |
| 7 | 5'-CGG GAA GCT TGT GTT GCA CCA T | SEQ ID NO. 14 |
| 8 | 5'-CGG GAA GCT TAG ACG CTA GTG T | SEQ ID NO. 15 |
| 9 | 5'-CGG GAA GCT TTA GCT AGC AGA C | SEQ ID NO. 16 |
| 10 | 5'-CGG GAA GCT TCA TGA TGC TAC C | SEQ ID NO. 17 |
| 11 | 5'-CGG GAA GCT TAC TCC ATG ACT C | SEQ ID NO. 18 |

3' primers

| | | |
|---|---|---|
| A | 5'-GCG CAA GCT TTT TTT TTT TTC T | SEQ ID NO. 19 |
| B | 5'-GCG CAA GCT TTT TTT TTT TTC C | SEQ ID NO. 20 |
| C | 5'-GCG CAA GCT TTT TTT TTT TTC G | SEQ ID NO. 21 |
| D | 5'-GCG CAA GCT TTT TTT TTT TTG T | SEQ ID NO. 22 |
| E | 5'-GCG CAA GCT TTT TTT TTT TTG G | SEQ ID NO. 23 |
| F | 5'-GCG CAA GCT TTT TTT TTT TTG A | SEQ ID NO. 24 |
| G | 5'-GCG CAA GCT TTT TTT TTT TTA T | SEQ ID NO. 25 |
| H | 5'-GCG CAA GCT TTT TTT TTT TTA C | SEQ ID NO. 26 |
| J | 5'-GCG CAA GCT TTT TTT TTT TTA G | SEQ ID NO. 27 |
| K | 5'-GCG CAA GCT TTT TTT TTT TTA A | SEQ ID NO. 28 |
| L | 5'-GCG CAA GCT TTT TTT TTT TTA A | SEQ ID NO. 29 |
| M | 5'-GCG CAA GCT TTT TTT TTT TTG C | SEQ ID NO. 30 |

Both sets of primers have a *Hind*III restriction site (AAGCTT) to facilitate subcloning.

*Fig. 2*

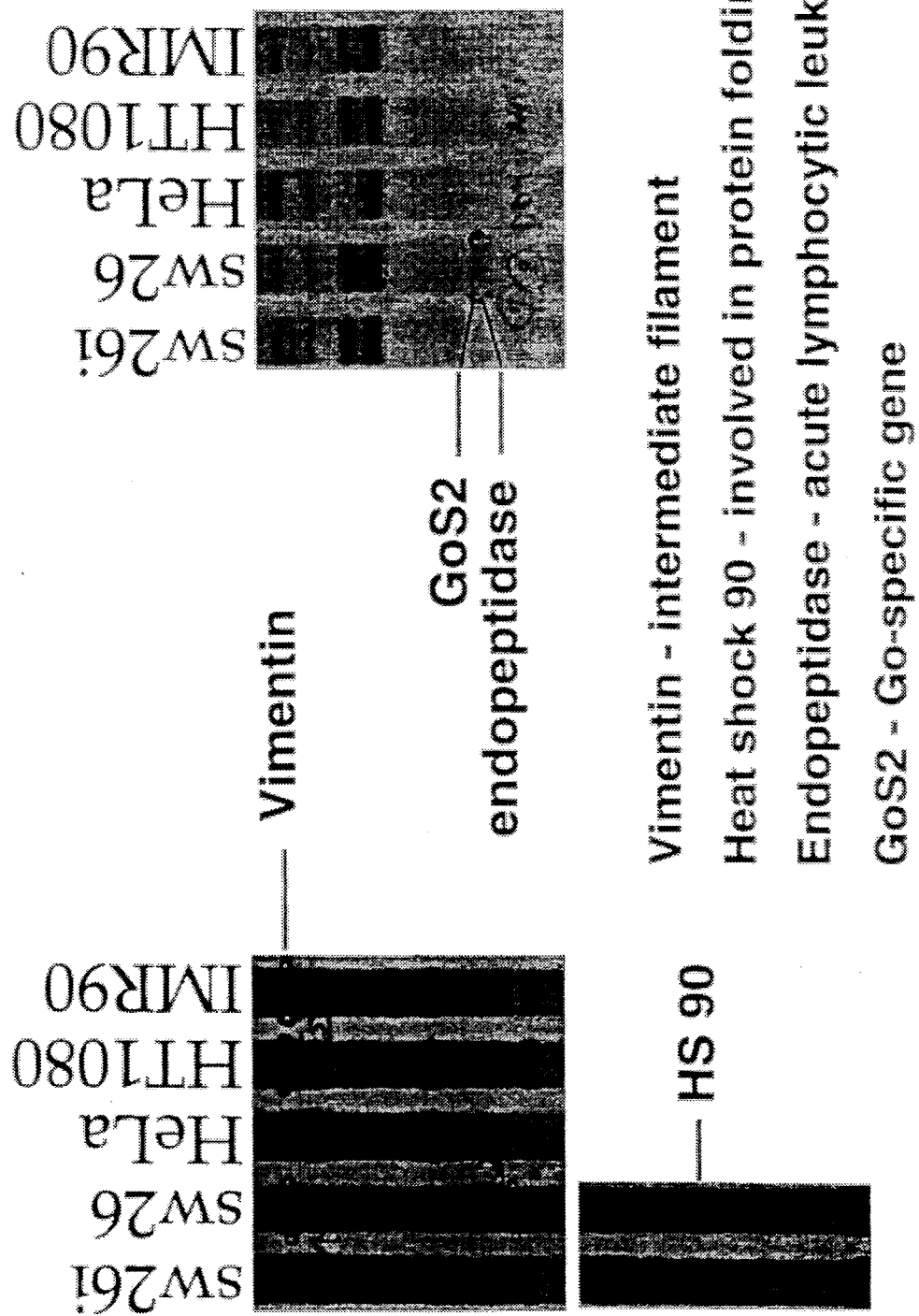

OC1 - appears to be a novel gene that is regulated by T antigen
OC2 - Tissue inhibitor of metalloprotenases (TIMP) - is up-regulated with age
1C1 - t-PA gene that is up-regulated with age
1C2 - is a novel gene that is down-regulated with age 5,580,726

SEQUENCE LISTING ( 1 ) GENERAL INFORMATION:

( i i i ) NUMBER OF SEQUENCES: 30

( 2 ) INFORMATION FOR SEQ ID NO: 1:

( i ) SEQUENCE CHARACTERISTICS:
        ( A ) LENGTH: 6
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for dA, dG, dC or deoxythymidylate ("dT")

( i i ) SEQUENCE DESCRIPTION: SEQ ID NO: 1:

T T T T N N         6

( 2 ) INFORMATION FOR SEQ ID NO: 2:

( i ) SEQUENCE CHARACTERISTICS:
        ( A ) LENGTH: 14
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for dA, dG, dC or deoxythymidylate ("dT")

( i i ) SEQUENCE DESCRIPTION: SEQ ID NO: 2:

A A A A A A A A A A   A A N N         1 4

( 2 ) INFORMATION FOR SEQ ID NO: 3:

( i ) SEQUENCE CHARACTERISTICS:
        ( A ) LENGTH: 12
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for dA, dG, dC or deoxythymidylate ("dT")

( i i ) SEQUENCE DESCRIPTION: SEQ ID NO: 3:

T T T T N N G G T A   C T         1 2

( 2 ) INFORMATION FOR SEQ ID NO: 4:

( i ) SEQUENCE CHARACTERISTICS:
        ( A ) LENGTH: 12
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for dA, dG, dC or deoxythymidylate ("dT")

(i i) SEQUENCE DESCRIPTION: SEQ ID NO: 4:

AAAANNCCAT GA                                                                                          12

(2) INFORMATION FOR SEQ ID NO: 5:

(i) SEQUENCE CHARACTERISTICS:
        (A) LENGTH: 12
        (B) TYPE: nucleic acid
        (C) STRANDEDNESS: single
        (D) TOPOLOGY: linear (i x) FEATURE:
        (D) OTHER INFORMATION: The letter "N" stands for dA, dG, dC or
        deoxythymidylate ("dT")

(i i) SEQUENCE DESCRIPTION: SEQ ID NO: 5:

TTTTNNGGTA CT                                                                                          12

(2) INFORMATION FOR SEQ ID NO: 6:

(i) SEQUENCE CHARACTERISTICS:
        (A) LENGTH: 12
        (B) TYPE: nucleic acid
        (C) STRANDEDNESS: single
        (D) TOPOLOGY: linear (i x) FEATURE:
        (D) OTHER INFORMATION: The letter "N" stands for dA, dG, dC or
        deoxythymidylate ("dT")

(i i) SEQUENCE DESCRIPTION: SEQ ID NO: 6:

AAAANNCCAT GA                                                                                          12

(2) INFORMATION FOR SEQ ID NO: 7:

(i) SEQUENCE CHARACTERISTICS:
        (A) LENGTH: 22
        (B) TYPE: nucleic acid
        (C) STRANDEDNESS: single
        (D) TOPOLOGY: linear (i i) SEQUENCE DESCRIPTION: SEQ ID NO: 7:

CGGGAAGCTT ATCGACTCCA AG                                                                               22

(2) INFORMATION FOR SEQ ID NO: 8:

(i) SEQUENCE CHARACTERISTICS:
        (A) LENGTH: 22
        (B) TYPE: nucleic acid
        (C) STRANDEDNESS: single
        (D) TOPOLOGY: linear (i i) SEQUENCE DESCRIPTION: SEQ ID NO: 8:

CGGGAAGCTT TAGCTAGCAT GG                                                                               22

(2) INFORMATION FOR SEQ ID NO: 9:

(i) SEQUENCE CHARACTERISTICS:
        (A) LENGTH: 22
        (B) TYPE: nucleic acid
        (C) STRANDEDNESS: single
        (D) TOPOLOGY: linear (i i) SEQUENCE DESCRIPTION: SEQ ID NO: 9:

CGGGAAGCTT GCTAAGACTA GC                                                                               22

(2) INFORMATION FOR SEQ ID NO: 10:

( i ) SEQUENCE CHARACTERISTICS:
    ( A ) LENGTH: 22
    ( B ) TYPE: nucleic acid
    ( C ) STRANDEDNESS: single
    ( D ) TOPOLOGY: linear ( i i ) SEQUENCE DESCRIPTION: SEQ ID NO: 10:

CGGGAAGCTT TGCAGTGTGT GA                                                       22

( 2 ) INFORMATION FOR SEQ ID NO: 11:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 11:

CGGGAAGCTT GTGACCATTG CA                                                       22

( 2 ) INFORMATION FOR SEQ ID NO: 12:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 12:

CGGGAAGCTT GTCTGCTAGG TA                                                       22

( 2 ) INFORMATION FOR SEQ ID NO: 13:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 13:

CGGGAAGCTT GCATGGTAGT CT                                                     22

( 2 ) INFORMATION FOR SEQ ID NO: 14:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 14:

CGGGAAGCTT GTGTTGCACC AT                                                     22

( 2 ) INFORMATION FOR SEQ ID NO: 15:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 15:

CGGGAAGCTT AGACGCTAGT GT                                                     22

( 2 ) INFORMATION FOR SEQ ID NO: 16:

( i ) SEQUENCE CHARACTERISTICS:

( A ) LENGTH: 22
( B ) TYPE: nucleic acid
( C ) STRANDEDNESS: single
( D ) TOPOLOGY: linear ( i i ) SEQUENCE DESCRIPTION: SEQ ID NO: 16:

CGGGAAGCTT TAGCTAGCAG AC        22

( 2 ) INFORMATION FOR SEQ ID NO: 17:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) SEQUENCE DESCRIPTION: SEQ ID NO: 17:

CGGGAAGCTT CATGATGCTA CC        22

( 2 ) INFORMATION FOR SEQ ID NO: 18:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) SEQUENCE DESCRIPTION: SEQ ID NO: 18:

CGGGAAGCTT ACTCCATGAC TC        22

( 2 ) INFORMATION FOR SEQ ID NO: 19:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) SEQUENCE DESCRIPTION: SEQ ID NO: 19:

GCGCAAGCTT TTTTTTTTT CT        22

( 2 ) INFORMATION FOR SEQ ID NO: 20:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) SEQUENCE DESCRIPTION: SEQ ID NO: 20:

GCGCAAGCTT TTTTTTTTT CC        22

( 2 ) INFORMATION FOR SEQ ID NO: 21:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) SEQUENCE DESCRIPTION: SEQ ID NO: 21:

GCGCAAGCTT TTTTTTTTT CG        22

( 2 ) INFORMATION FOR SEQ ID NO: 22:

( i ) SEQUENCE CHARACTERISTICS:
( A ) LENGTH: 22
( B ) TYPE: nucleic acid ( C ) STRANDEDNESS: single
( D ) TOPOLOGY: linear ( i i ) SEQUENCE DESCRIPTION: SEQ ID NO: 22:

GCGCAAGCTT TTTTTTTTTT GT 22

( 2 ) INFORMATION FOR SEQ ID NO: 23:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) SEQUENCE DESCRIPTION: SEQ ID NO: 23:

GCGCAAGCTT TTTTTTTTTT GG 22

( 2 ) INFORMATION FOR SEQ ID NO: 24:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) SEQUENCE DESCRIPTION: SEQ ID NO: 24:

GCGCAAGCTT TTTTTTTTTT GA 22

( 2 ) INFORMATION FOR SEQ ID NO: 25:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) SEQUENCE DESCRIPTION: SEQ ID NO: 25:

GCGCAAGCTT TTTTTTTTTT AT 22

( 2 ) INFORMATION FOR SEQ ID NO: 26:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) SEQUENCE DESCRIPTION: SEQ ID NO: 26:

GCGCAAGCTT TTTTTTTTTT AC 22

( 2 ) INFORMATION FOR SEQ ID NO: 27:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) SEQUENCE DESCRIPTION: SEQ ID NO: 27:

GCGCAAGCTT TTTTTTTTTT AG 22

( 2 ) INFORMATION FOR SEQ ID NO: 28:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) SEQUENCE DESCRIPTION: SEQ ID NO: 28:

GCGCAAGCTT TTTTTTTTT AA 22

( 2 ) INFORMATION FOR SEQ ID NO: 29:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 29:

GCGCAAGCTT TTTTTTTTT CA 22

( 2 ) INFORMATION FOR SEQ ID NO: 30:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 30:

GCGCAAGCTT TTTTTTTTT GC 22

METHOD AND KIT FOR ENHANCED DIFFERENTIAL DISPLAY

BACKGROUND OF THE INVENTION

The field of the present invention relates to techniques for screening differences in gene expression between various cell types or between different stages of cell development.

In higher organisms, every cell expresses about 10–20% of the 100,000 possible different genes. Gene expression is involved in all life processes, such as development, aging and disease states. Thus, the analysis of which genes are expressed at any given time, and the identification of the expressed mRNAs, is of prime interest in molecular biology.

One such method for screening differences in gene expression is known as Differential Display. This method is described in Pardee et al., U.S. Pat. No. 5,262,311, hereby incorporated by reference. Differential Display involves amplifying partial cDNA sequences from subsets of mRNAs by reverse transcription and the polymerase chain reaction (PCR), then displaying these sequences on a sequencing gel.

In the Differential Display method, the primers which hybridize to the 3' end of the mRNA [the 3' primers] are selected to take advantage of the polyadenylate [polyA] tail present on most eukaryotic mRNAs to anchor the primers at the 3' end of the mRNA. Each 3' primer hybridizes to a portion of the polyA tail and additionally to 2 bases which are immediately 5' of the polyA tail. The 2 nucleotides of the 3' primer which are not complementary to the polyA tail are of the sequence VN, where V is deoxyadenylate ("dA"), deoxyguanylate ("dG"), or deoxycytidylate ("dC"), and N, the 3' terminal nucleotide, is dA, dG, dC, or deoxythymidylate ("dT"). By probability, each 3' primer will recognize one-twelfth of the total mRNA population, since there are twelve different combinations of the two 3' bases, eliminating T as the base which hybridizes immediately 5' of the polyA tail. Such primers are used to reverse transcribe specific subpopulations of mRNAs.

A second set of primers, the 5' primers, is designed to randomly select a subset of the cDNAs generated using the 3' oligonucleotide primers. The 5' primers are of arbitrary base sequence. The cDNA sequences defined by these two primer sets are then amplified by PCR. The amplified products can then be displayed on a sequencing gel, and visualized by autoradiography. Using this method, comparisons can be made of the genes expressed by different cell types, or by cells in various stages of development or disease.

Differential Display uses short 9 to 14 base primers that require low temperature annealing throughout PCR amplification. Such low temperature annealing conditions result in a decline in the reproducibility of the method. As noted by the creators of Differential Display (Liang et al., Nucl. Acids Res. 21:3269–3275), "[a] troublesome aspect of the method is that the noise level of false positives, though a few percent, can be very appreciable relative to the truly different bands between cells."

SUMMARY OF THE INVENTION

Applicant provides an improved method of Differential Display, named Enhanced Differential Display (EDD). EDD is designed as a technique for screening differences in gene expression between various cell types or between different stages of cell development. The technique is highly reproducible, leading to precise typing of the expressed genes in any given cell. EDD analysis permits the identification of novel genes involved in differentiation, aging, and disease, and enables direct comparisons of different cell types and disease states.

EDD uses the polymerase chain reaction (PCR) to amplify cDNA produced from a selected set of expressed mRNA sequences from particular cell types. The EDD method is similar to Differential Display, which also uses reverse transcriptase and PCR to identify differentially expressed genes. However, unlike Differential Display, which uses short 9 to 14 bases primers, EDD uses longer primers.

We have surprisingly found that by using longer primers, and/or an alteration in the annealing temperatures, the number of false positives can be significantly reduced. By "longer primers" it is meant that the primers are of at least 21 nucleotides in length, and can be up to 50 nucleotides in length. Most preferably, the oligonucleotide primers are between 22 and 30 nucleotides in length.

Thus, in a first aspect, the invention features an improved method for detecting differences in gene expression which comprises, first, contacting nucleic acid which comprises an mRNA sequence with a first oligonucleotide primer, wherein said first oligonucleotide primer has a hybridizing sequence sufficiently complementary to a region of said mRNA to hybridize therewith. Next, the first oligonucleotide primer is extended in an extension reaction using the mRNA as a template to give a first DNA primer extension product complementary to the mRNA. The first DNA primer extension product is then contacted with a second oligonucleotide primer, wherein the second oligonucleotide primer has a hybridizing sequence sufficiently complementary to the first DNA primer extension product to hybridize therewith. The second oligonucleotide primer is then extended in an extension reaction using the first DNA primer extension product as a template to give a second DNA primer extension product complementary to the first DNA primer extension product, and the first and second DNA primer extension products are amplified. The improvements of this method comprise one or more of the following: providing first and second oligonucleotide primers with a length of at least 21 oligonucleotides; the use of a two-step PCR amplification; and, not adding additional 3' oligonucleotide primers to the PCR amplification reaction mixture.

In a preferred embodiment, the PCR amplification is carried out in two steps. The first one to four cycles of PCR are carried out under non-stringent conditions. By "non-stringent" conditions it is meant that low annealing temperatures are used. Preferably, the annealing temperature used for the non-stringent conditions cycles is between 35° C. and 45° C. Most preferably, the annealing temperature used for the non-stringent conditions cycles is about 41° C. The next 16 to 20 cycles of amplification are carried out in stringent conditions. By "stringent" conditions it is meant that higher annealing temperatures are used. Preferably, the annealing temperature used for the stringent conditions cycles is between 55° C. and 70° C. Most preferably, the annealing temperature used for the stringent conditions cycles is about 60° C.–65° C. The buffer conditions used for both the stringent and non-stringent cycles are the same. An example of the annealing conditions used for both the stringent and nonstringent cycles is: 1 µl cDNA (3'primer carried over from cDNA), 2 µl 10x PCR buffer, 1.5 µl 0.1 mM dNTP, 1.25 µl 20 µM 5'primer, 1 µl 1 to 5 dilution of alpha-$^{32}$P dATP, 0.5 µl Taq polymerase, and 12.75 µl dH$_2$O.

"Cycle" refers to the process which results in the production of a copy of a target nucleic acid. A cycle includes a denaturing step, an annealing step, and an extending step. An example of the non-stringent PCR cycles is: denature the DNA at 94° C., for 45 sec.; anneal the primers at 41° C., for 1 min.; extend the primers at 72° C., for 1 min. An example of the stringent PCR cycles is: denature the DNA at 94° C., for 45 sec.; anneal the primers at 60° C., for 1 min.; extend the primers at 72° C., for 1 min.

In another preferred embodiment, a portion of the 3' oligonucleotide primer hybridizes to the polyA tail of the mRNA sequence. Preferably, the 3' oligonucleotide primer has at least one nucleotide which can hybridize to an mRNA sequence which is immediately 5' to the polyA tail. More preferably, the 3' oligonucleotide is at least 21 nucleotides in length, and contains two nucleotides which can hybridize to a mRNA sequence which is immediately 5' to the polyA tail, and the remaining portion of the 3' oligonucleotide can hybridize to the polyA tail. Most preferably, the 3' oligonucleotide is at least 21 nucleotides in length, and contains two nucleotides which can hybridize to a mRNA sequence which is immediately 5' to the polyA tail, and the middle 10–15 bases of the 3' oligonucleotide can hybridize to the polyA tail, while the 5' end of the 3' oligonucleotide contains a restriction site.

In another embodiment, 3' oligonucleotide primers which do not hybridize to the polyA tail of mRNA can be used. In this embodiment, mRNA having a polyA tail is first isolated from total cellular RNA. A random set of 10–15 primers is used to hybridize to different regions of the mRNA.

In another preferred embodiment, no additional 3' oligonucleotide primers are added to the PCR amplification reaction mixture. The amplification proceeds using only the 3' oligonucleotide primers which remain in the cDNA reaction mixture. The use of lower amounts of 3' oligonucleotide primers results in lowered production of non-specific sequences.

EDD was designed to eliminate false positives as well as to increase the efficiency of obtaining authentic differentially expressed genes. Long primers and the two-stage PCR amplification appear to eliminate totally the problem of false positives and the subsequent labor-intensive work to verify true positives. Moreover, PCR amplification is highly efficient with EDD. In addition, when a preferred embodiment of the method is used, the amplified gene fragments are easily subcloned into bacterial vectors owing to the restriction sites designed into the 5' end of the primers.

Freedom from false positives is especially important when comparing many tissues simultaneously, such as is done when screening for senescent-specific genes. FIG. 4 shows an example of EDD performed on RNA from 11 different cell samples at different stages of senescence and immortalization. Since the chances of false positives increase with the number of samples being compared, a comparison such as this would not be very informative using standard Differential Display. By contrast, we have identified many authentic differentially expressed genes using EDD on these 11 samples.

With the increased accuracy and reproducibility of EDD, catalogues of expressed genes can be prepared from different cell types during aging, development, and disease. These catalogues can then be used to identify rapidly most of the genes involved in the processes. Therefore, EDD represents a significant advance in our technical capability to identify novel genes likely to be functionally important in aging, development, and disease states.

DESCRIPTION OF THE PREFERRED EMBODIMENTS

The drawings will first be briefly described.

Drawings FIG. 1 depicts the basic method of EDD.

FIG. 2 depicts typical primer sets used in the basic EDD method.

FIG. 3 depicts PCR products from differentially expressed genes which are displayed simultaneously on a DNA sequencing gel and visualized by autoradiography.

The method of the present invention is generally described above. Below are non-limiting examples depicting this method.

The EDD method can be used as follows to screen differences in gene expression. First, cDNA is prepared from total cellular RNA using twelve different 22-base oligonucleotide primers (3' oligos, see FIG. 2) that are targeted to the poly A tail of pol II mRNA transcripts. The last two bases of each primer varies so as to anchor the primer to the 3' end of different sets of mRNAs. A second set of ten 22-base oligo primers (the 5' oligos, see FIG. 2) is designed to randomly select a subset of cDNAs from each of the twelve 3' primers. PCR amplification of a subset of cDNAs is carried out in a two step process using particular 5' and 3' primers. The first 2–4 cycles are carried out with annealing temperature of 41° C. which allows degenerate priming with the 3'-terminal 5 to 7 bases of each primer. The next 18 to 20 cycles of amplification are carried out with a 60° C. annealing temperature to give specific annealing of all 22 bases in each primer.

Figure 1:
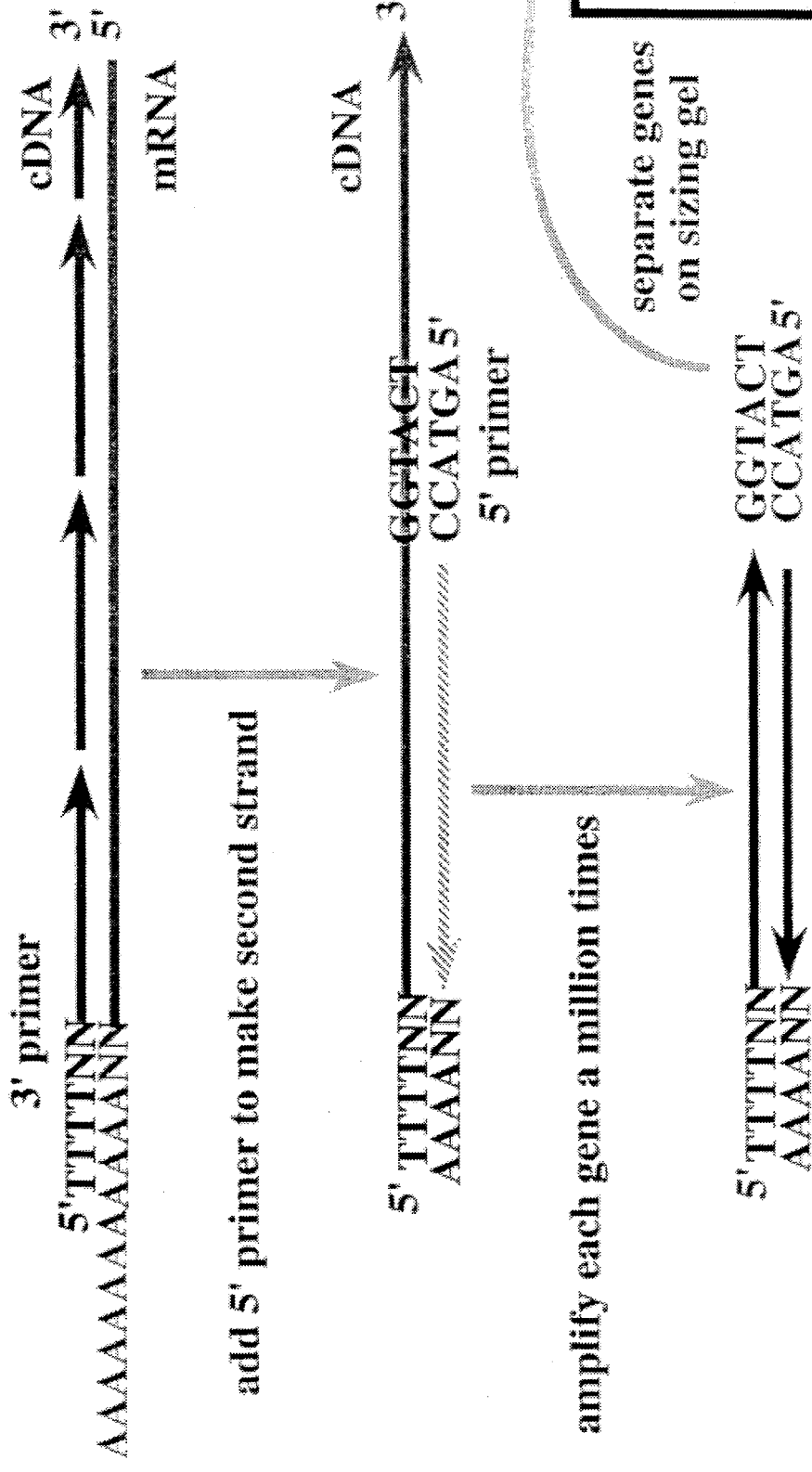
Figure 4:
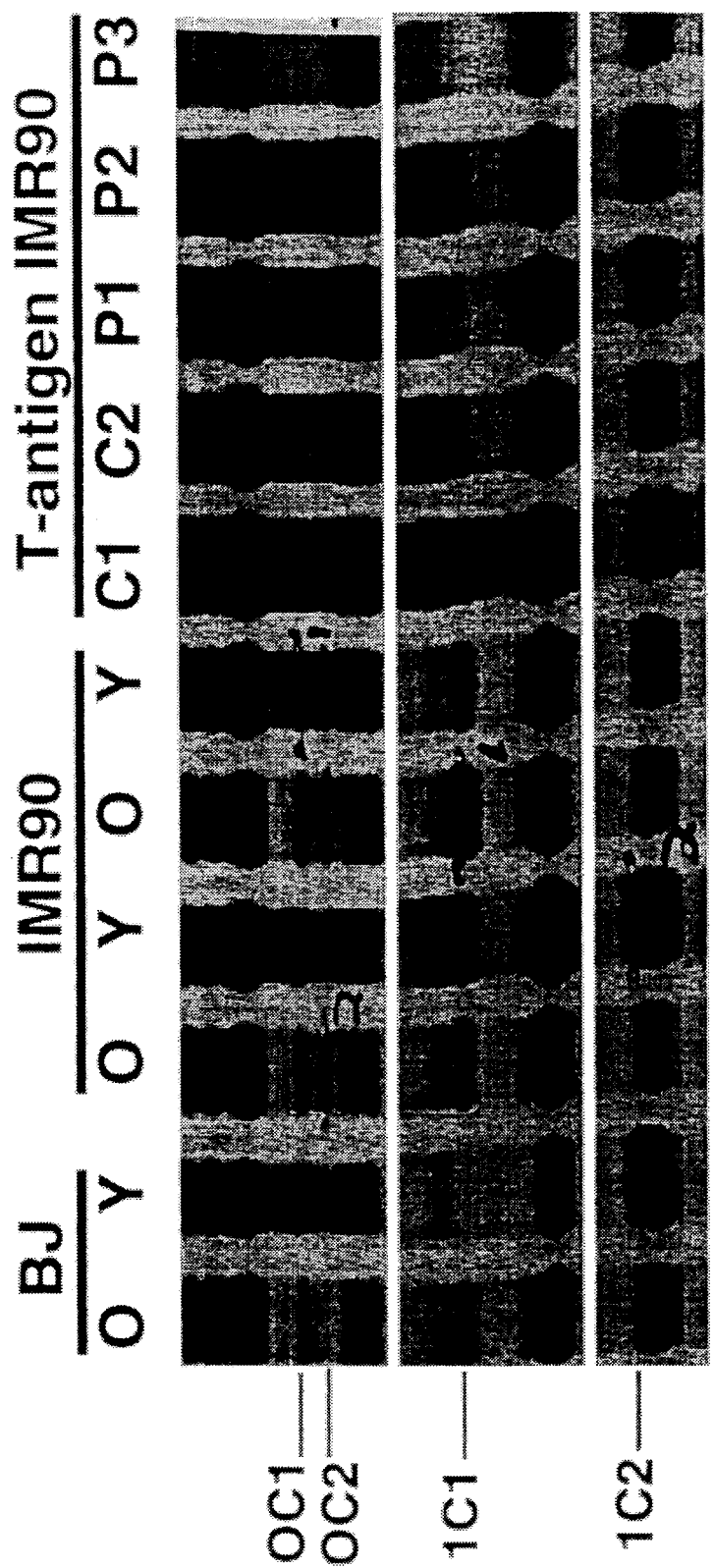
FIG. 4 depicts an example of EDD performed on RNA from 11 cell samples at different stages of senescence and immortalization.

The PCR products can be labeled by including alpha-$^{32}$P dATP in the reaction mixture. The $^{32}$P-labeled PCR products from many cell types are then displayed simultaneously on a DNA sequencing gel and visualized by autoradiography (FIG. 3–4). Each lane contains hundreds of expressed genes specific to the particular 5' and 3' primers used and can be directly compared to the cDNA samples in adjacent lanes that were amplified with the same oligo primer set using RNA from different cell types. When differences in band intensity are observed in adjacent lanes, the up- or down-regulated gene fragments can be cut out of the gel and amplified by PCR. The amplified gene products can then be directly sequenced or rapidly subcloned into a plasmid vector for DNA sequencing. The DNA sequence can be used to search GENBANK to determine whether the gene is a known or novel gene. The full-length cDNA copy of novel genes can be isolated by screening a lambda gt11 library with labeled probes made to the EDD gene fragment.

In a further aspect, the invention comprises a kit for performing the above method. Such a kit may be prepared from readily available materials and reagents.

The following examples demonstrate the mechanism and utility of the present invention. They are not limiting and should not be considered as such.

Example 1: Synthesis of the cDNA

The cDNA copies of RNA are produced using the following procedure.
Annealing reaction:
 Mix: 1 μg total RNA
 2.5 μl 20 μM 3'primer (dT$_{12}$mer)
 dH$_2$O to 13 μl
 Heat for 10 min. at 75° C. cool on ice for 7 min.
Elongation reaction:
 The following reagents are added to the above mix:

5 μl 5x first strand synthesis buffer
1 μl RNAsin (Promega, or Pharmacia)
2.5 μl 0.1M DTT
2.5 μl 1 mM dNTP
1 μl Reverse Transcriptase (M-MLV, BRL)
Incubate for 70 min. at 37° C.
Heat to inactivate enzyme for 10 min. at 95° C.
The reaction mixture can be stored at −20° C. for later use.

Example 2: PCR amplification of cDNA

The cDNA copies produced in example 1 are amplified as follows.

Mix: 1 μl 1 cDNA (3'primer carried over from cDNA)
2 μl 10x PCR buffer
1.5 μl 0.1 mM dNTP
1.25 μl 20 μM 5'primer
1 μl 1 to 5 dilution of alpha-$^{32}$P dATP
0.5 μl Taq polymerase
12.75 μl dH$_2$O
Run PCR for 4 cycles at 94° C., 45 sec.
41° C., 1 min.
72° C., 1 min.
and 18 cycles at 94° C., 45 sec.
60° C., 1 min.
72° C., 1 min.

Example 3: Sequencing gel analysis

The PCR amplified cDNA produced in example 2 can be analyzed on a sequencing gel as follows.

3 μl PCR product from example 2 is mixed with 2 μl running dye (Formamide dye). The samples are heated for 3 min. at 80°–90° C. and loaded on a 6% sequencing gel (1xTBE) and the gel is run at 2000 V (or the current <50 mA). The gels are run until the second dye reaches the bottom. This can be varied depending on the size range of the mRNA which is being compared. The gel is then dried down, and the gel and the film are taped together. Holes are carefully punched at three corners of the gel, and the film is exposed overnight.

Example 4: Recovery of the differentially displayed bands

The dried gel and the autoradiograph are lined up, and a needle is used to mark the differential bands to be cut. The bands are then cut out using a razor blade. It is important to rinse the razor blade between each band to avoid cross contamination. The gel slide is transferred into a 1.5 ml microfuge tube, and 1 ml TE is added. Next, the TE, the strips of the Saran wrap, and the Whatman paper are taken off. 40 μl of the elution buffer (TE+100 mM NaCl) is added to the gel slice, and it is heated for 10 min. at 95° C., and incubate at room temperature overnight.

Example 5: Reamplification of recovered bands

The bands recovered in example 4 can be amplified as follows.

Mix: 2–5 μl of overnight gel slice mix
5 μl 10x PCR buffer
2.5 μl 1 mM dNTP
3 μl 20M 5'primer
3 μl 20 μM 3'primer
1 μl Taq polymerase
dH$_2$O to 50 μl
Run PCR for 24 to 30 cycles at 94° C., 45 sec.
60° C., 1 min.
72° C., 1 min.
When cycles are completed, extend for 5 more min. at 72° C.

At this point the PCR products can either be subcloned into a vector or purified from LMP agarose gel and sequenced from the 5' primer by a PCR sequencing kit (Stratagene).

Example 6: Use of EDD to identify genes that are specifically expressed in young or senescent cells An initial catalog was made for RNA isolated form young and senescent cells, using 144 primer combinations, made up from 12 different 3'-T rich primers and 12 arbitrary 5' primers. The analysis of the information generated by this process showed that:
1) EDD is reproducible. Samples were analyzed with the same primer set several times within the span of several months, generating the same interpretable results.
2) Great care should be taken with all reagents. cDNA, primers and nucleotides should be aliqouted at the time of preparation, stored at −20° C. and not be thawed more than a few times.
3) The 3' primer plays a major role in determining the quality of the EDD. In the conditions used, most 3' T rich primers gave consistently good results, independent of the 5' primer that was used.
The primers ending in T12-CT and T12-AT gave poor results.
The primers ending in T12-AA, T12-AC and T12-AG gave results of mixed quality.
The primers ending in T12-CC, T12-CG, T12-GT, T12-GG T12-GA, T12-CA and T12-GC gave excellent results.
It was also shown that the pen-ultimate base in the 3' primer does contribute to its specificity, and that different display patterns are obtained if different primers are used that only differ in the pen-ultimate base.
4) In summary, out of the possible 144 combinations, 85 were deemed interpretable. On average, it is possible to identify 50 bands per lane. Therefore, the first catalog was an investigation of about 4250 gene-tags.
5) From the information obtained so far by searching GenBank, most of the known RNA sequences found to be differentially expressed by EDD have already been identified as young or senescent expressed RNAs by conventional assays published by others. Moreover, Northern blots have confirmed the EDD analysis of differential expression in the case of the novel genes tested.
6) With the conditions that were used (42° C. annealing), the specificity of annealing by the 5' primer is determined by 7 out of the last 8 bases at the 3'primer end (22 sequences analyzed). Using 7 out of 8 bases as the determinant of specificity and all 3' primers, the following probability for detecting a desired gene sequence in a 300 base pair stretch is found:
use of 10 different 5' primers: 69%
use of 15 different 5' primers: 83%
use of 20 different 5' primers: 90%
Thus, a nearly complete catalog of all expressed genes can be prepared using a large enough set of primer combinations.

7) The genes or gene-tags identified in the above screen can be investigated for their use as markers of senescence. It also anticipated that these genes can be used for the development of novel therapeutics. For instance, young genes might be growth factors, extra-cellular matrix proteins or receptors. The re-administering (in whatever form) of these kinds of gene products could themselves prove to be treatments for agerelated diseases. Senescent specific genes could, for instance, be receptors, (anti-)growth factors or extra-cellular matrix proteins. Inhibition of expression of such genes is a possible therapeutic for age-related diseases.

8) The discovered markers (gene-tags) can also be used for the identification of novel compounds that alter or modulate the pattern of senescent gene expression.

Other embodiments are within the following claims.

We claim:

1. Method for detecting different stages of cell development or detecting differences in gene expression comprising the steps of:
   a) contacting mRNA from each of said cell populations in separate reaction vessels with a first oligonucleotide primer, wherein said first oligonucleotide primer has a hybridizing sequence sufficiently complementary to a region of said mRNA to hybridize therewith,
   b) extending said first oligonucleotide primer in an extension reaction using the mRNA as a template to give a first DNA primer extension product complementary to the mRNA,
   c) contacting said first DNA primer extension product with a second oligonucleotide primer, wherein said second oligonucleotide primer has a hybridizing sequence sufficiently complementary to said first DNA primer extension product to hybridize therewith,
   d) extending said second oligonucleotide primer in an extension reaction using the first DNA primer extension product as a template to give a second DNA primer extension product complementary to the first DNA primer extension product,
   e) amplifying said first and second DNA primer extension products in a polymerase chain reaction comprising cycles of primer annealing, extension and denaturation, at an annealing temperature of between 35° and 45° for at least two and not more than four cycles, then
   f) amplifying said first and second DNA primer extension products at an annealing temperature of between 55° and 70° for at least 16 cycles, to provide amplified gene sequences
   g) separating said amplified gens sequences by size and/or charge; and
   h) comparing amplified gens sequences separated in step (g) to detect an amplified gene sequence from one of said cell populations that is present at a different level in the other of said cell populations;

wherein said first and second oligonucleotide primers comprise at least 21 nucleotides.

2. The method of claim 1 wherein a mixture of two or more first primers is used.

3. The method of claim 1 wherein a mixture of two or more second primers is used.

4. The method of claim 1 wherein a mixture of two or more first primers and a mixture of two or more second primers are used.

5. The method of claim 1 wherein said first and second oligonucleotide primers consist of from 21 to 50 oligonucleotides.

6. The method of claim 1 wherein said first oligonucleotide primer contains a restriction site.

7. The method of claim 1 wherein said second oligonucleotide primer contains a restriction site.

8. The method of claim 4 wherein said first oligonucleotide primer hybridizes to a region of mRNA comprising a portion of a 3' polyadenosine tail of said mRNA and at least one nucleotide 5' to said 3'polyadenosine tail.

9. The method of claim 4 wherein said first primers are selected from the group consisting of

5'-GCG CAA GCT TTT TTT TTT TTC T-3' (SEQ ID NO. 19);

5'-GCG CAA GCT TTT TTT TTT TTC C-3' (SEQ ID NO- 20);

5'-GCG CAA GCT TTT TTT TTT TTC G-3' (SEQ ID NO. 21);

5'-GCG CAA GCT TTT TTT TTT TTG T-3' (SEQ ID NO- 22);

5'-GCG CAA GCT TTT TTT TTT TTG G-3' (SEQ ID NO. 23);

5'-GCG CAA GCT TTT TTT TTT TTG A-3' (SEQ ID NO- 24);

5'-GCG CAA GCT TTT TTT TTT TTA T-3' (SEQ ID NO. 25);

5'-GCG CAA GCT TTT TTT TTT TTA C-3' (SEQ ID NO, 26);

5'-GCG CAA GCT TTT TTT TTT TTA G-3' (SEQ ID NO. 27);

5'-GCG CAA GCT TTT TTT TTT TTA A-3' (SEQ ID NO. 28);

5'-GCG CAA GCT TTT TTT TTT TTC A-3' (SEQ ID NO. 29); and,

5'-GCG CAA GCT TTT TTT TTT TTG C-3' (SEQ ID NO. 30).

10. The method of claim 4 wherein said first primers are selected from the group consisting of

5'-GCG CAA GCT TTT TTT TTT TTC C-3' (SEQ ID NO. 20);

5'-GCG CAA GCT TTT TTT TTT TTC G-3' (SEQ ID NO. 21);

5'-GCG CAA GCT TTT TTT TTT TTG T-3' (SEQ ID NO. 22);

5'-GCG CAA GCT TTT TTT TTT TTG G-3' (SEQ ID NO. 23);

5'-GCG CAA GCT TTT TTT TTT TTG A-3' (SEQ ID NO. 24);

5'-GCG CAA GCT TTT TTT TTT TTA C-3' (SEQ ID NO. 26);

5'-GCG CAA GCT TTT TTT TTT TTA G-3' (SEQ ID NO. 27);

5'-GCG CAA GCT TTT TTT TTT TTA A-3' (SEQ ID NO. 28);

5'-GCG CAA GCT TTT TTT TTT TTC A-3' (SEQ ID NO. 29); and,

5'-GCG CAA GCT TTT TTT TTT TTG C-3' (SEQ ID NO. 30).

11. The method of claim 4 wherein said first primers are selected, from the group consisting of

5'-GCG CAA GCT TTT TTT TTT TTC C-3' (SEQ ID NO. 20);

5'-GCG CAA GCT TTT TTT TTT TTC G-3' (SEQ ID NO. 21);

5'-GCG CAA GCT TTT TTT TTT TTG T-3' (SEQ ID NO. 22);

5'-GCG CAA GCT TTT TTT TTT TTG G-3' (SEQ ID NO. 23);

5'-GCG CAA GCT TTT TTT TTT TTG A-3' (SEQ ID NO. 24);

5'-GCG CAA GCT TTT TTT TTT TTC A-3' (SEQ ID NO. 29); and,

5'-GCG CAA GCT TTT TTT TTT TTG C-3' (SEQ ID NO. 30).

12. The method of claim 4 wherein each of said second primers comprises a region of randomly selected nucleotides.

13. The method of claim 12 wherein said second primers differ from each other in the region of randomly selected nucleotides.

14. The method of claim 4 wherein said second primers are selected from the group consisting of:

5'-CGG GAA GCT TAT CGA CTC CAA G -3' (SEQ ID NO. 7);

5'-CGG GAA GCT TTA GCT AGC ATG G-3' (SEQ ID NO. 8);

5'-CGG GAA GCT TGC TAA GAC TAG C-3' (SEQ ID NO. 9);

5'-CGG GAA GCT TTG CAG TGT GTG A-3' (SEQ ID NO. 10);

5'-CGG GAA GCT TGT GAC CAT TGC A-3' (SEQ ID NO. 11);

5'-CGG GAA GCT TGT CTG CTA GGT A-3' (SEQ ID NO. 12);

5'-CGG GAA GCT TGC ATG GTA GTC T-3' (SEQ ID NO. 13);

5'-CGG GAA GCT TGT GTT GCA CCA T-3' (SEQ ID NO. 14);

5'-CGG GAA GCT TAG ACG CTA GTG T-3' (SEQ ID NO. 15);

5'-CGG GAA GCT TTA GCT AGC AGA C-3' (SEQ ID NO. 16);

5'-CGG GAA GCT TCA TGA TGC TAC C-3' (SEQ ID NO. 17); and,

5'-CGG GAA GCT TAC TCC ATG ACT C - 3' (SEQ ID NO. 18).

* * * * *

UNITED STATES PATENT AND TRADEMARK OFFICE
CERTIFICATE OF CORRECTION

PATENT NO. : 5,580,726
DATED : December 3, 1996
INVENTOR(S) : Bryant Villeponteau, Junli Feng, Walter Funk, Maarten H.K. Linskens It is certified that error appears in the above-indentified patent and that said Letters Patent is hereby corrected as shown below:

Column 5, line 51: delete "slide" and add —slice—

Column 5, line 60: add —then— before be

Column 17, line 61: delete "gens" and add —gene—

Column 17, line 64: delete "gens" and add —gene—

Signed and Sealed this

Eighteenth Day of March, 1997

Attest:

BRUCE LEHMAN

*Attesting Officer*  Commissioner of Patents and Trademarks